US00PP22562P2

(12) United States Plant Patent

Gomez Bullis

(10) Patent No.: US PP22,562 P2

(45) Date of Patent: Mar. 6, 2012

(54) *NEOREGELIA* PLANT NAMED 'VALENTINES'

(50) Latin Name: ***Neoregelia carolinae*×*Neoregelia meyenoorfii***
Varietal Denomination: Valentines

(75) Inventor: Patricia E. Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 3 days.

(21) Appl. No.: 12/806,815

(22) Filed: Aug. 21, 2010

(51) Int. Cl.
*A01H 5/00* (2006.01)

(52) U.S. Cl. ..... Plt./370

(58) Field of Classification Search ..... Plt./370
See application file for complete search history.

*Primary Examiner* — June Hwu

(74) *Attorney, Agent, or Firm* — C. A. Whealy

(57) ABSTRACT

A new and distinct cultivar of *Neoregelia* plant named 'Valentines', characterized by its upright and outwardly arching growth habit; broad glossy green and pale yellow green bi-colored lower leaves; broad glossy dark red purple-colored upper leaves; and good interiorscape and landscape performance.

1 Drawing Sheet

Botanical designation: *Neoregelia carolinae*×*Neoregelia meyenoorfii*.

Cultivar denomination: 'VALENTINES'.

BACKGROUND OF THE INVENTION

The present invention relates to a new and distinct cultivar of *Neoregelia* plant, botanically known as *Neoregelia carolinae*×*Neoregelia meyenoorfii*, and hereinafter referred to by the name 'Valentines'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2002 in Princeton, Fla. of an unnamed proprietary selection of *Neoregelia carolinae*, not patented, as the female, or seed, parent with *Neoregelia meyenoorfii* 'Rivera', not patented, as the male, or pollen, parent. The new *Neoregelia* plant was discovered and selected by the Inventor as a single plant within the progeny of the stated cross-pollination in a controlled greenhouse environment in Princeton, Fla. in 2002.

Asexual reproduction of the new *Neoregelia* plant by offsets in a controlled environment in Princeton, Fla. since 2003, has shown that the unique features of this new *Neoregelia* plant are stable and reproduced true to type in successive generations.

SUMMARY OF THE INVENTION

Plants of the new *Neoregelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Valentines'. These characteristics in combination distinguish 'Valentines' as a new and distinct cultivar of *Neoregelia:*

1. Upright and outwardly arching growth habit.
2. Broad glossy green and pale yellow green bi-colored lower leaves.
3. Broad glossy dark red purple-colored upper leaves.
4. Good interiorscape and landscape performance.

Plants of the new *Neoregelia* differ primarily from plants of the female parent selection in the following characteristics:

1. Plants of the new *Neoregelia* have broader leaves than plants of the female parent selection.
2. Plants of the new *Neoregelia* and the female parent selection differ in leaf color as plants of the female parent selection have orange-colored upper leaves.

Plants of the new *Neoregelia* differ primarily from plants of the male parent, 'Rivera', in the following characteristics:

1. Plants of the new *Neoregelia* have broader leaves than plants of 'Rivera'.
2. Plants of the new *Neoregelia* and 'Rivera' differ in leaf color as plants of 'Rivera' have green-colored leaves tinged with burgundy.

Plants of the new *Neoregelia* can be compared to plants of the *Neoregelia* 'Flandria', not patented. In side-by-side comparisons conducted in Princeton, Fla., plants of the new *Neoregelia* and 'Flandria' differed primarily in the following characteristics:

1. Plants of the new *Neoregelia* had broader leaves than plants of 'Flandria'.
2. Leaves of plants of the new *Neoregelia* have blunter apices than leaves of plants of 'Flandria'.

BRIEF DESCRIPTION OF THE PHOTOGRAPHS

The accompanying colored photographs illustrate the overall appearance of the new *Neoregelia* plant showing the colors as true as it is reasonably possible to obtain in colored reproductions of this type. Colors in the photographs may differ slightly from the color values cited in the detailed botanical description which accurately describe the colors of the new *Neoregelia* plant.

The photograph at the bottom of the sheet is a side perspective view of a typical flowering plant of 'Valentines' grown in a container.

The photograph at the top of the sheet is a top perspective view of a typical flowering plant of 'Valentines'.

DETAILED BOTANICAL DESCRIPTION

The aforementioned photographs and following observations, measurements and values describe flowering plants grown during the spring in 15-cm containers in a polypropylene-covered greenhouse in Princeton, Fla. under commercial *Neoregelia* production practices. During the production of the plants, day temperatures ranged from 10° C. to 32° C., night temperatures ranged from 7° C. to 32° C. and light levels averaged 3,200 foot-candles. Plants were one year old when the photographs and description were taken. In the following description, color references are made to The Royal Horticultural Society Colour Chart, 2007 Edition, except where general terms of ordinary dictionary significance are used.

Botanical classification: *Neoregelia carolinae*×*Neoregelia meyenoorfii* 'Valentines'.

Parentage:

*Female, or seed, parent.*—Unnamed proprietary selection of *Neoregelia carolinae*, not patented.

*Male, or pollen, parent.*—*Neoregelia meyenoorfii* 'Rivera', not patented.

Propagation:

*Type.*—By offsets.

*Time to initiate roots, summer.*—About 30 to 45 days at 28° C. to 30° C.

*Time to initiate roots, winter.*—About 45 to 60 days at 18° C. to 22° C.

*Time to produce a rooted young plant, summer.*—About three months at 28° C. to 30° C.

*Time to produce a rooted young plant, winter.*—About four months at 18° C. to 22° C.

*Root description.*—Medium in thickness, fibrous; yellow to tan in color.

*Rooting habit.*—Moderately freely branching; medium density.

Plant description:

*Plant form/growth habit.*—Upright and outwardly arching growth habit; rosette leaves are erect when young, becoming outwardly arching with development; plants readily produce uniform offsets; vigorous growth habit.

*Plant height.*—About 23 cm.

*Plant diameter or spread.*—About 50 cm.

*Internode length.*—About 3 mm.

*Stem texture.*—Smooth, glabrous.

*Stem color.*—Close to 155D.

Foliage description:

*Arrangement.*—Rosette, spiral phyllotaxis; simple; sessile, clasping.

*Shape.*—Oblong.

*Apex.*—Cuspidate.

*Base.*—Truncate.

*Margin.*—Senate, spinose.

*Length.*—About 32 cm.

*Width, mid-section.*—About 7.8 cm.

*Width, base.*—About 10.4 cm.

*Texture.*—Smooth, glabrous; leathery; longitudinally ribbed.

*Luster.*—Glossy.

*Venation pattern.*—Parallel.

*Color.*—Lower leaves, upper surface: Center, close to 137A; longitudinal marginal stripes, close to 150D; towards the base, close to 157C; venation, close to 137A. Lower leaves, lower surface: Center, close to 137B; longitudinal marginal stripes, close to 150D; venation, close to 137B. Upper leaves, upper surface: Center, close to 60B; occasional longitudinal stripes, close to 150D; towards the base, close to 157C; venation, close to 60B. Upper leaves, lower surface: Center, close to 60C; towards the base, close to 157C; venation, close to 60C.

Inflorescence description:

*Inflorescence form.*—Terminal flat-topped compact corymb located inside the leaf rosette; about 95 flowers develop per inflorescence.

*Time to flower.*—Plants begin flowering about nine to eleven weeks after planting; plants flower naturally during the spring in Florida.

*Flower longevity.*—Individual flowers last about one day on the plant; flowers persistent.

*Fragrance.*—None detected.

*Inflorescence length.*—About 6.3 cm.

*Inflorescence diameter.*—About 4.2 cm.

*Flower size.*—Length: About 4.8 cm. Diameter: About 6 mm.

*Flower buds.*—Length: About 4.3 cm. Diameter: About 5 mm. Shape: Narrowly elongate. Color: Close to 91C.

*Petals.*—Quantity per flower: Three in a single whorl. Shape: Oblanceolate. Apex: Acuminate. Base: Truncate. Margin: Entire. Length: About 3.7 cm. Width: About 7 mm. Texture: Smooth, glabrous. Color: When opening, upper surface: Close to NN155D; towards the apex, close to 92A. When opening, lower surface: Close to NN155D; towards the apex, close to 92B to 92C. Fully opened, upper surface: Close to NN155D; towards the apex, close to 92B. Fully opened, lower surface: Close to NN155D, towards the apex, close to 92C to 92D.

*Flower bracts.*—Quantity per flower: One. Shape: Elliptical. Length: About 3 cm. Width: About 8 mm. Texture: Membraneous. Color: Close to 157D.

*Sepals.*—Quantity per flower: Three in a single whorl. Shape: Oblanceolate. Apex: Acuminate. Base: Truncate. Margin: Entire. Length: About 2.4 cm. Width: About 6 mm. Texture: Smooth, glabrous. Color, upper surface: Close to 157C to 157D. Color, lower surface: Close to 157D.

*Peduncles.*—Length: About 7 mm. Diameter: About 1.3 cm. Strength: Strong. Aspect: Typically erect. Texture: Smooth, glabrous. Color: Close to NN155A.

*Pedicels.*—Length: About 1 cm. Diameter: About 3 mm. Strength: Strong. Aspect: Typically erect to somewhat outward and curving upright. Texture: Smooth, glabrous. Color: Close to NN155C.

*Stamens.*—Quantity per flower: Six. Filament length: About 1.7 cm; partially adnate to the petals. Filament color: Close to NN155D. Anther shape: Lanceolate. Anther length: About 5 mm. Anther color: Close to 158D. Pollen amount: Scarce. Pollen color: Close to 158B.

*Pistils.*—Quantity per flower: One. Pistil length: About 3.8 cm. Stigma shape: Oval, elongated. Stigma color: Close to 155D. Style length: About 2.2 cm. Style color: Close to NN155D. Ovary color: Close to NN155C.

*Fruit/seed.*—Fruit and seed production have not been observed on plants of the new *Neoregelia*.

Temperature tolerance: Plants of the new *Neoregelia* have been observed to tolerate temperatures ranging from about 2° C. to about 37° C.

Interior & garden performance: Plants of the new *Neoregelia* have been observed to have good postproduction longevity under interior conditions and to have good garden performance. Plants of the new *Neoregelia* have been observed to tolerate summer rains.

Disease/pest resistance: Resistance to pathogens and pests common to *Neoregelia* plants has not been observed.

It is claimed:

1. A new and distinct *Neoregelia* plant named 'Valentines' as illustrated and described.

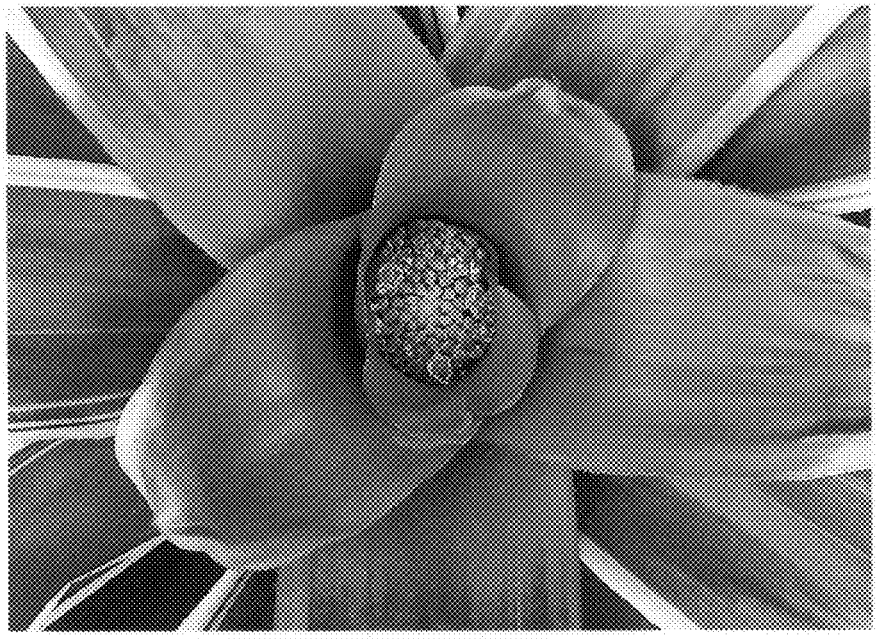
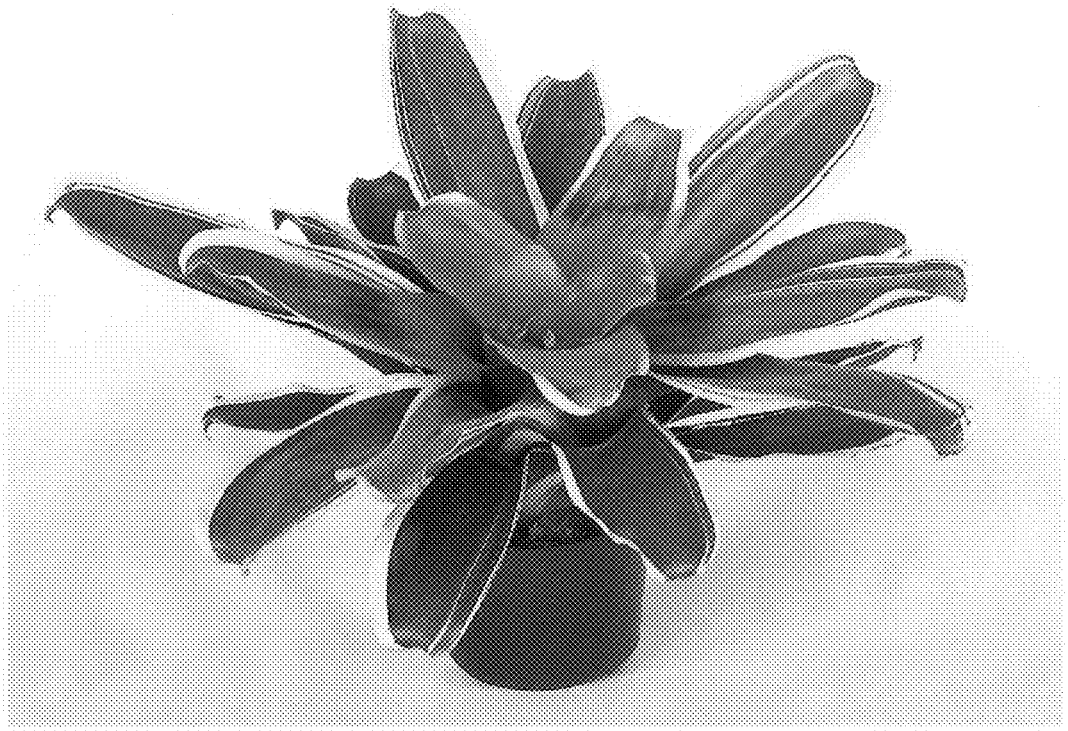

* * * * *